US005726030A

United States Patent [19]
Ollar et al.

[11] Patent Number: 5,726,030
[45] Date of Patent: Mar. 10, 1998

[54] METHOD FOR AUTOMATICALLY TESTING THE ANTIBIOTIC SENSITIVITY OF A PARAFFINOPHILIC MICROORGANISM

[75] Inventors: Robert A. Ollar, Milford; Mitchell S. Felder, Sharon, both of Pa.

[73] Assignee: Infectech, Inc., Sharon, Pa.

[21] Appl. No.: 673,877

[22] Filed: Jul. 2, 1996

Related U.S. Application Data

[62] Division of Ser. No. 535,873, Aug. 28, 1995, Pat. No. 5,637,501.

[51] Int. Cl.$^6$ .............................. C12Q 1/24; C12Q 1/04
[52] U.S. Cl. ..................... 435/30; 435/34; 435/287.9; 435/288.3
[58] Field of Search .................... 435/30, 34, 36, 435/40, 287.19, 288.1, 288.3, 801, 863

[56] References Cited

U.S. PATENT DOCUMENTS

| | | | |
|---|---|---|---|
| 3,826,717 | 7/1974 | Gilbert et al. | |
| 3,928,140 | 12/1975 | Wyatt et al. | 195/103.5 R |
| 4,324,859 | 4/1982 | Saxholm | 435/33 |
| 4,683,195 | 7/1987 | Mullis et al. | |
| 4,683,201 | 7/1987 | Hamill et al. | |
| 4,683,202 | 7/1987 | Mullis | |
| 5,153,119 | 10/1992 | Ollar | |
| 5,316,918 | 5/1994 | Ollar | |
| 5,472,877 | 12/1995 | Ollar | 435/288.1 |
| 5,569,592 | 10/1996 | Ollar | 435/32 |
| 5,637,501 | 6/1997 | Ollar et al. | 435/286.2 |

OTHER PUBLICATIONS

Wallace, J.M. et al., "*Mycobacterium avium* Complex Infection In Patients With The Acquired Immunodeficiency Syndrome* A Clinicopathologic Study", *Chest*, 93 (5), pp. 926–932 (1988).

Wolinsky, E., "Nontuberculous Mycobacteria And Associated Diseases", *American Review of Respiratory Disease*, vol. 119:107–159 (1979).

Horsburgh, C.R., Jr. et al., "Disseminated Infection with *Mycobacterium avium–intracellulare*", *Medicine*, vol. 64, No. 1:36–48 (1983).

Horsburgh, C.R., Jr. et al., "The Epidemiology Of Disseminated Nontuberculous Mycobacterial Infection In The Acquired Immunodeficiency Syndrome (AIDS)", *American Review of Respiratory Disease*, 139:4–7 (1989).

Reichert, C.M. et al., "Pathologic Features Of Aids", *AIDS: Etiology, Diagnosis, Treatment and Prevention*, pp. 111 and 134, J.B. Lippincott Company (1985).

Hawkins, C.C. et al., "*Mycobacterium avium* Complex Infections In Patients With The Acquired Immunodeficiency Syndrome", *Annals of Internal Medicine*, 105:184–188 (1986).

Hoy, J. et al. "Quadruple–Drug Therapy For *Mycobacterium avium–intracellulare* Bacteremia In AIDS Patients", *The Journal of Infectious Diseases*, 161:801–805 (Apr. 1990).

Fuhs, G.W., "Der Mikrobielle Abbau Von Kohlenwasserstoffen", *Arch. Mikrobiol.*, 39:374–422 (1961).

Mishra, S.K. et al., "Observations On Paraffin Baiting As A Laboratory Diagnostic Procedure In Nocardiosis", *Mycopathologica and Mycologia Applicatia*, vol. 51, 2–3, pp. 147–157 (1973).

Ollar, R.–A., "A Paraffin Baiting Technique That Enables A Direct Microscopic View Of in situ Morphology Of *Nocardia asteroides* With The Acid–Fast Or Fluorescence Staining Process", *Zbl. Bakt. Hyg., I. Abt. Orig. A 234*, pp. 81–90 (1976).

Kemper, C.A. et al., "Microbiologic And Clinical Response Of Patients With AIDS and MAC Bacteremia To A Four Oral Drug Regimen", *American Society for Microbiology*, (Abstract), p. 297 (1990).

Klatt, E.C. et al., "Pathology Of *Mycobacterium avium–intracellulare* Infection In Acquired Immunodeficiency Syndrome", *Human Pathology*, vol. 18, No. 7: 709–714 (Jul. 1987).

Bermudez, L.E. et al., "An Animal Of *Mycobacterium avium* Complex Disseminated Infection After Colonization Of The Intestinal Tract", *The Journal of Infectious Diseases*, 165:75–79 (Jan. 1992).

Murphey, S.A. et al., "*Mycobacterium Avium–Intracellulare* In A Hospital Hot Water System: Epidemiologic Investigation", *American Society for Microbiology*, 277 (1983).

Ma, P. et al., "Definitive Diagnostic Methods For Diseases Indicative Of AIDS", *AIDS and Infections of Homosexual Men*, Second Edition, pp. 233–234 Butterworth Publishers (1989).

Havlik, J.A., Jr. et al., "Disseminated *Mycobacterium avium* Complex Infection: Clinical Identification And Epidemiologic Trends", *The Journal of Infectious Diseases*, 165:577–580 (Mar. 1992).

(List continued on next page.)

*Primary Examiner*—Ralph Gitomer
*Attorney, Agent, or Firm*—David V. Radack; Eckert Seamans Cherin & Mellott, LLC

[57] ABSTRACT

A method of automatically testing the sensitivity of a paraffinophilic microorganism to different antimicrobial agents and concentrations thereof includes a plurality of receptacles each containing an amount of liquid medium, an antimicrobial agent to be tested and the microorganism to be tested. A paraffin containing slide is placed in each receptacle after which incubation is effected. A light scatter sensor is employed to automatically and sequentially monitor the extent of microorganism growth on the slides and the growth on each slide is employed to determine which antimicrobial agent and which concentration is effective to resist growth of the paraffinophilic microorganism. The slides are moved sequentially in operative relationship with the light scatter sensor while resisting rotational movement of the slides. Positive and negative control slides are preferably employed as is a computer in receiving and processing the results of the slide testing. Related apparatus is disclosed.

13 Claims, 3 Drawing Sheets

OTHER PUBLICATIONS

Inderlied, C.B. et al., "Disseminated *Mycobacterium avium* Complex Infection", *AIDS Clinical Review*, pp. 165–191 (1990).

Gonzalez, R. et al., "Evaluation Of Gen–Probe DNA Hybridization Systems For The Identification Of *Mycobacterium tuberculosis* And *Mycobacterium avium–intracellulare*", *Diagn. Microbiol. Infect. Dis.*, 8:69–77 (1987).

Ollar, R.–A. et al., "The Use Of Paraffin Wax Metabolism In The Speciation Of *Mycobacterium avium–intracellulare*", *Tubercle*, 71, pp. 23–28, Longman Group UK, Ltd. (1990).

Kemper, C.A. et al., "Treatment Of *Mycobacterium avium* Complex Bacteremia In AIDS With A Four–Drug Oral Regimen", *Annals of Internal Medicine*, 116, No. 6:466–472 (Mar. 1992).

Heifets, L. et al., "Comparison Of Bactericidal Activities Of Streptomycin, Amikacin, Kanamycin, And Capreomycin Against *Mycobacterium avium* And *Mycobacterium tuberculosis*", *Antimicrobial Agents and Chemotherapy*, pp. 1298–1301 (Aug. 1989).

Hurley, S.S. et al., "Development Of A Diagnostic Test For Johne's Disease Using a DNA Hybridization Probe", *Journal Of Clinical Microbiology*, pp. 1582–1587 (1989).

Kirihara, J.M. et al., "Improved Detection Times For *Mycobacterium avium* Complex And *Mycobacterium tuberculosis* With The BACTEC Radiometric System", *Journal of Clinical Microbiology*, pp. 841–845 (Nov. 1985).

Ollar R., The Use of Paraffin Wax Metabolism in the Speciation of Mycobacterium avium–intracellulare, Tubercle 71 23–28, 1990.

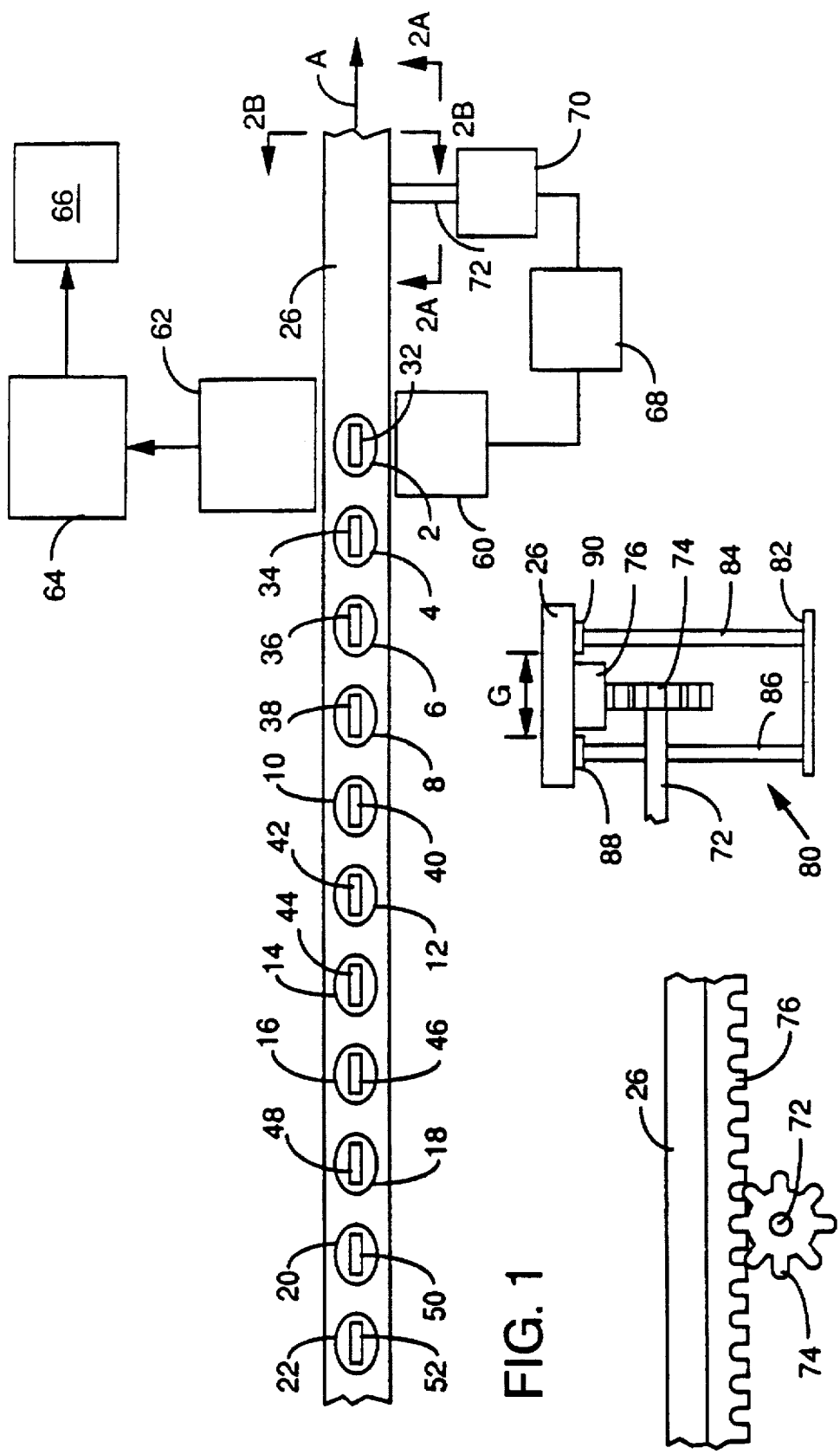

METHOD FOR AUTOMATICALLY TESTING THE ANTIBIOTIC SENSITIVITY OF A PARAFFINOPHILIC MICROORGANISM

This is a division, of application Ser. No. 08/535,873, filed Sep. 28, 1995 now U.S. Pat. No. 5,637,501.

BACKGROUND OF THE INVENTION

1. Field of the Invention

The present invention relates to a method and associated apparatus for and/or determining antibiotic sensitivity of a paraffinophilic microorganism and, more specifically, the invention relates to expediting information regarding a more rapid and effective treatment of a patient.

2. Description of the Prior Art

It has been found that more than 80% of the acquired immunodeficiency syndrome ("AIDS") patients have MAI (Mycobacterium avium-intracellulare) present in their bodies. Wallace, J. M. and Hannah, J. B., "Mycobacterium avium Complex in Patients with Acquired Immunodeficiency Syndrome-A Clinicopathologic Study", Chest 93(5): 926-932 (1988).

Organisms of MAI prior to the AIDS epidemic were recognized as a rare form of pneumonia in patients with chronic lung infections (E. Wolinsky, *Nontuberculous mycobacteria and associated diseases.* Am. Rev. Respir. Dis. 1979, 119:107-59). Organisms of MAI comprise two closely related species, *M. avium* and *M. intracellulare*, which have minor virulence in the non-HIV host. By 1980, only 24 cases of MAI had been reported in the medical literature (C. R. Horsburgh, Jr. et al., Disseminated infection with Mycobacterium avium intracellulare. Medicine (Baltimore) 1985, 64:36-48). However, the epidemic of disseminated MAI infection is concurrent with the AIDS epidemic.

It has been known to test antibiotics in different concentrations against a microorganism to determine if the antibiotics will inhibit growth of the microorganism and in what antibiotic concentrations. See U.S. Pat. No. 3,826,717.

It has been known to determine drug efficacy against a paraffinophilic microorganism by confirming a lack of colony growth on a paraffin slide. See Ollar, A Modified Broth Dilution Assay for Antibiotic Sensitivity Testing of *Mycobacterium Avium-intracellulare* Using Paraffin Slide Cultures," Tubercle 72, pp. 198-205 (1991).

U.S. Pat. No. 5,316,918 discloses method and apparatus for determining the antibiotic sensitivity of Mycobacterium avium intracellulare (MAI) to different antimicrobial agents and dosages thereof. In this patent, a plurality of test tubes each contain an amount of an antimicrobial agent to be tested and MAI complex organisms to be assayed. A separate paraffin coated slide is placed in each test tube and incubation is effected, after which, the MAI complex organism growth on the slides at discrete time intervals is observed in order to permit determination of the minimum inhibitory concentration of the antimicrobial agent necessary to resist the MAI complex organism growth on the slides. The disclosure of this patent is incorporated herein by reference.

As will be apparent from the foregoing, it is vital to human health that MAI be treated as early as possible (C. A. Kemper et al., California Collaborative Group; Microbiologic and clinical response of patients with AIDS and MAC bacteremia to a four oral drug regimen; In: Program and abstracts of the 30th Interscience Conference on Antimicrobial Agents and Chemotherapy; Atlanta, Oct. 21-24, 1990; Washington D.C.; Am. Society for Microbiology; 1990; 297. abstract).

While the foregoing systems have made major advances in respect of antibiotic sensitivity testing, there remains a substantial need for methods and apparatus for enhancing a degree of automation and the resultant speed of processing specimens in order to determine the antibiotic sensitivity of paraffinophilic organisms in order to facilitate more rapid and effective treatment of patients.

There is a real and substantial need for improved means of rapidly determining the antibiotic sensitivity of MAI and other paraffinophilic organisms.

SUMMARY OF THE INVENTION

The present invention has met the above-described need. In one embodiment, it provides a method of automatically testing the sensitivity of a paraffinophilic microorganism to different antimicrobial agents, such as antibiotics, and concentrations thereof, by providing a plurality of receptacles, each containing an amount of liquid medium, an antimicrobial agent to be tested and the microorganism to be tested. In each of the receptacles is placed a slide containing a paraffin source. The receptacles are then incubated, after which a light scatter sensing means automatically and sequentially monitors the extent of microorganism growth on the slides. The extent of colony growth is employed to determine which antimicrobial agent in which concentration is effective to resist growth of the microorganism. A preferred light scatter sensing means is a nephelometer.

The automated apparatus associated with the method of sensitivity testing preferably includes a plurality of receptacles, a plurality of paraffin coated slides to be inserted into the receptacles in the presence of a liquid medium, the microorganism to be tested, and a quantity of an antimicrobial agent. Means are provided for incubating the tubes. Means are provided for sequentially moving the slides into operative relationship with respect to light scatter sensing means. The light scatter sensing means are provided for automatically sequentially monitoring light scatter of the slides and outputting information with respect to the extent of growth on the microorganisms on each slide.

The method and apparatus may be employed on both paraffinophilic microorganisms.

In a preferred practice of the apparatus of this invention, means are provided to translate the slides while resisting rotational movement thereof, and preferably to translate them within receptacles which are fixedly secured to a carrier which is transported in a path which passes by the scatter light sensing means.

Computer processor means are preferably employed to receive output from the light scatter sensing means and provide an output indicative of the identity of the antimicrobial agent and concentration to which the organism is sensitive.

It is an object of the present invention to provide an automated system for a rapid determination of the antibiotic sensitivity of a paraffinophilic microorganism to different antimicrobial agents and concentrations thereof.

It is a further object of the present invention to provide such an automated system which may be employed with paraffinophilic microorganisms.

It is a another object of the present invention to provide such an automated system which is cost effective and adapted for use by relatively unskilled laboratory personnel.

These and other objects of the invention will be more fully understood from the following description of the invention on reference to the illustrations appended hereto.

BRIEF DESCRIPTION OF THE DRAWINGS

FIG. 1 is a partially schematic plan view of a form of apparatus employed in the automated system of the present invention.

FIG. 2A is a cross-sectional illustration of a portion of the drive apparatus taken through 2A—2A of FIG. 1.

FIG. 2B is a cross-sectional illustration of a portion of the carrier assembly taken through 2B—2B of FIG. 1.

DESCRIPTION OF THE PREFERRED EMBODIMENTS

Figure 5:
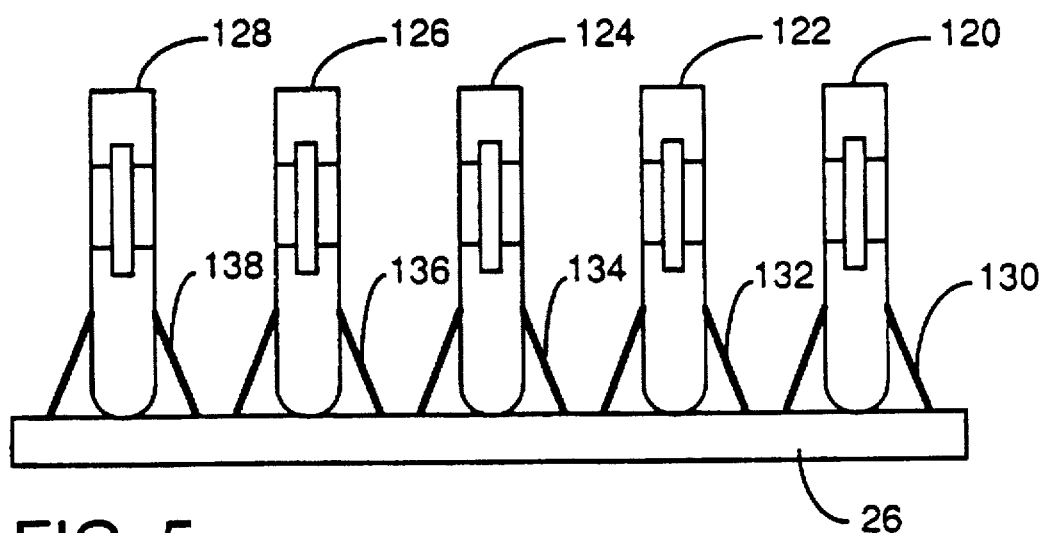
FIG. 5 is an elevational view of the test tube carrier means.

As used herein, the term "patient" refers to a member of the animal kingdom, including human beings, whose body specimen is being processed by the system of the present invention.

As used herein, the term "body specimen" shall include fecal matter, blood, sputum, tissue, and cerebral spinal fluid obtained from a patient.

As used herein, the term "paraffinophilic" means an organism that can employ paraffin as a source of carbon in a basal salt media, devoid of other forms of carbon. The organism may be bacterial or fungal in nature. The term shall expressly include, but not be limited to the following organisms: Micrococcus Paraffinae; Corynebacterium Simplex; Ahnl; Mycococcus (Rhodococcus) Cinnabareus; Ahnl, Mycococcus (Rhodoc) Rhodochrous; Mycobact, Perrugosum Var. Athanicum; Mycobact, Rubrum Var. Propanicum; Mycobacterium Hyalinum; Mycobacterium Lacticola; Mycobacterium Album, M. Luteum; Mycobacterium Microti; Mycobacterium Murinum; Mycobacterium Rubrum, Mycobacterium Phlei.; Mycobacterium Phlei, M. Smegmatis; Mycobacterium Testudo; Mycobacterium Avium-Intracellulare; Nocardia Spp.; Actinomyces; Candida Lipolytica; Candida Tropicalis, Torulopsis Colliculosa; Monilia Sp., Hansenula Sp., Torula rossa; Penicillium Sp.; Aspergillus Flavus; Aspergillus sp., Penicillium Sp.; Citromyces Sp., Scopulariopsis Sp.; Pseudomonas Fluorescens Liquefaciens; Ahnl. Pem. Fluorescens Denitrificans; Pseudomonas Aeruginosa.

It will be appreciated from what follows that the rapid, automated system of the present invention facilitates prompt antibiotic sensitivity testing of a paraffinophilic microorganism. This facilitates more timely and effective patient treatment. Among the most important categories of such paraffinophilic organisms are the mycobacterium, candida and nocardia species. The method will identify an antimicrobial agent which will effectively inhibit growth of the paraffinophilic microorganism and will also determine the minimum concentration level of the antimicrobial agent which will inhibit such growth.

Referring specifically to FIG. 1, them is shown a preferred embodiment of the present invention usable in a method of automatically testing the sensitivity of a pure culture of a microorganism to different antimicrobial agents and concentrations thereof. In this embodiment, a microorganism, which may have been previously speciated as by the technique taught in U.S. Pat. No. 5,153,119, has been introduced into a plurality of receptacles, each containing an amount of liquid medium and antimicrobial agent to be tested. A paraffin slide is introduced into each of the receptacles which are subsequently incubated. The receptacles 2–22 (even numbers only) are fixedly secured to an elongated, substantially rigid movable carrier member 26, such that the receptacles 2–22 will be translated therewith in the direction shown by the arrow A. The carrier member 26 may be made of any suitable material, such as aluminum, steel, stainless steel, or resinous plastic, for example. The receptacles 2–22, respectively, contain slides 32–52 (even numbers only). The slides 32–52 are fixedly secured, respectively, within receptacles 2–22 which may test tubes. The slides 32–52 are generally oriented so as to have their elongated direction aligned with the direction of travel of the carrier 26. As the carrier moves in the direction of arrow A, the slides 2–22 will sequentially be positioned in operative relationship to the light scatter sensing means which consists of light source 60, which directs a light beam toward light detector 62. In the preferred embodiment, a beam of visible light from light source 60 will impinge upon slide 32, with the growth of the microorganism thereon producing a corresponding scatter of light which is received by the light receiving sensor 62 and converts the received light into an appropriate output electrical signal which will be delivered to computer means 64. The computer means 64, in turn, provides output to output means 66, which may conveniently be a display, such as a cathode ray tube or a hard copy printer, for example. The degree of light scatter will be related to the extent of microorganism growth with light scatter increasing as growth on the slide increases.

As each slide 32–52 progressively moves in front of the light beam emerging from light source 60, movement of the carder 26 is terminated to provide a period of dwell, which may be on the order of 2 to 10 seconds so as to provide an efficient reading. This movement is preferably effected by means of stepper motor 70, which by shaft 72, as shown in FIG. 2A, will cause rotary movement of fixedly secured spur gear 74 which is engaged within rack 76, which is secured to the undersurface of carrier member 26. It is preferred that the carrier 26 have capacity to receive about 4 to 6 slides although more may be employed, if desired. The slides may be so spaced on the carrier that a slide may be passed through the light scatter sensing means 62 with a dwell period of about 2 to 10 seconds. This will provide a processing speed of about 6 to 30 slides per minute. In a preferred embodiment, control means 68 is operatively associated with both light source 60 and stepper motor 70. Control means 68 energizes light source 60 to emit a light beam when the stepper motor 70 is not moving carrier member 26 with a slide 32–52 dwelling in front of light source 60.

Referring to FIG. 2B, an example of a suitable support 80 for slidably supporting carrier member 26 will be considered. The support means 80 may have a base 82 to which is secured a pair of spaced upwardly projecting support elements 84, 86 which have at their upper ends, respectively, enlarged feet 88, 90 which have upper surfaces in underlying sliding supportive relationship with the undersurface of carrier member 26. The gap G between feet 88, 90 will permit passage of rack 76 therebetween. If desired, the support means 80 may be continuous with the carrier member 26 or may be a plurality of individual support members spaced from each other.

It is preferred that one of the slides be a control slide. The control slide will preferably be a slide which has not been exposed to any antimicrobial agent and, therefore, would be a fully grown or positive control slide.

A convenient means of indexing each slide would be to permanently affix a number or letter or other identifying indicia on the carrier member 26 adjacent to each test tube position. In this manner, the slide identity may be correlated with the output of computer means 64.

The computer means 64 may be a general purpose digital microprocessor. It may be programmed in a manner readily known to those skilled in the art to sequentially compare the light scatter value of each slide 32–52 with that of a control slide and to provide an output to output means 66, such as a visual screen display or hard copy, with or without prior enhancement, which indicates the difference between the control slide and the specific slides containing the same pure culture of a paraffinophilic microorganism, but exposed to different concentrations of different or the same antimicrobial agents, such an antibiotics. In this manner, there is provided the minimal concentration level of a specific antimicrobial agent that must be used to control growth of the microorganism. Also, the minimum bactericidal concentration may be determined. This is the minimum inhibitory concentration (MIC) of the antimicrobial agent needed to inhibit the growth of a paraffinophilic microorganism. If desired, the computer means 64 may display or print out the values of the control slide and all other slides in a numerical or coded manner.

After a cycle of operation, the slides 32–52 and receptacles 2–22 may be removed from the carrier member 26 and the carrier member 26 moved back to a starting position for insertion of an additional plurality of receptacles containing slides. The movement would be in the opposite direction from the direction of arrow A in FIG. 1 and may be effected by reversing the stepping motor 70. The receptacles 2–22 may then be removed from carrier member 26 and a new cycle of operation initiated.

The preferred light scatter sensing means 60, 62 is a nephelometer. A suitable nephelometer is that sold by Beckman Instruments, Inc. of Fullerton, Calif.

Figure 3:
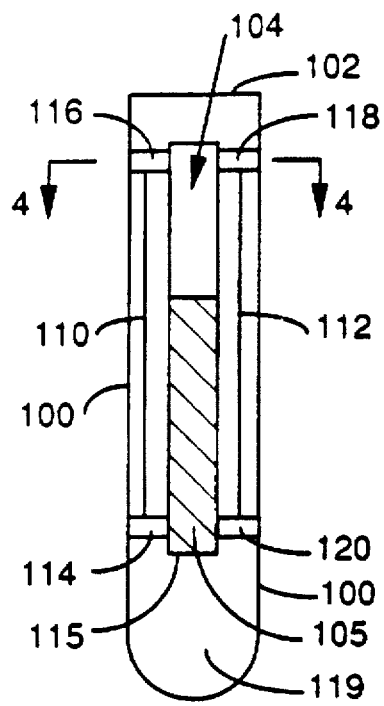
FIG. 3 is a cross-sectional elevational view of a test tube having a slide immobilized therein.
Figure 4:
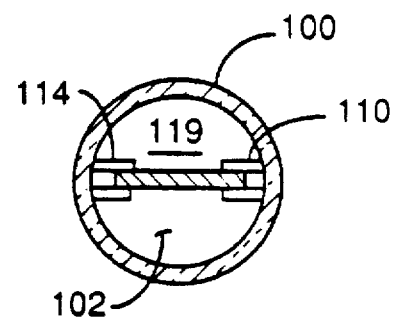
FIG. 4 is a cross-sectional illustration taken through 4—4 of FIG. 3 showing the slide immobilized within a test tube.

Referring to FIGS. 3 and 4, more details regarding the restraining means for the slides 32–52 and receptacles 2–22 (FIG. 1) will be considered. As shown in FIG. 3, a receptacle in the form of a test tube 100 has an upwardly disposed opening 102 and a slide 104 positioned therein. The slide 104 has a paraffin layer 105 covering a portion thereof on each side. Two pairs of generally aligned, channel-shaped retaining elements 116–118 and 114–120 each define a pair of opposed channels which receive the slide 104 and retain it in fixed position. For convenience of positioning in the form shown, a generally cylindrical base 119 is connected to and supports the channels 114, 120. The base member 119 is preferably of complimentary shape with respect to the lower portion of test tube 100 and is in surface to surface contact therewith. An upper portion of the base 119 has an upwardly open slot 115 which receives the lower portion of slide 105. The slide restraining means 114, 116, 118, 119, 120 are preferably formed as a unit and may conveniently be made of resinous plastic or metal, for example. Elements 114, 116 and 118, 120, respectively, are each joined by connectors 110, 112. It will be appreciated that while disposed in this position the slide 104 cannot be subjected to any rotational movement with respect to the receptacle 100. It will be appreciated that slides may be introduced into the receptacle 100 by longitudinal sliding movement.

Referring to FIG. 5, there is shown the carrier member 26 and a plurality of slide containing receptacles which, in the form shown, are upwardly open test tubes 120, 122, 124, 126, 128, each of which is fixedly secured within a clamp member 130–138 (even numbers only) which, in turn, are fixedly secured to the carrier member 26. In this manner, translational movement of the slides and the tubes 120–128, along with the carrier member 26 is facilitated while resisting any rotational movement of either the tube 120–128 or the slides disposed therein.

Figure 6:
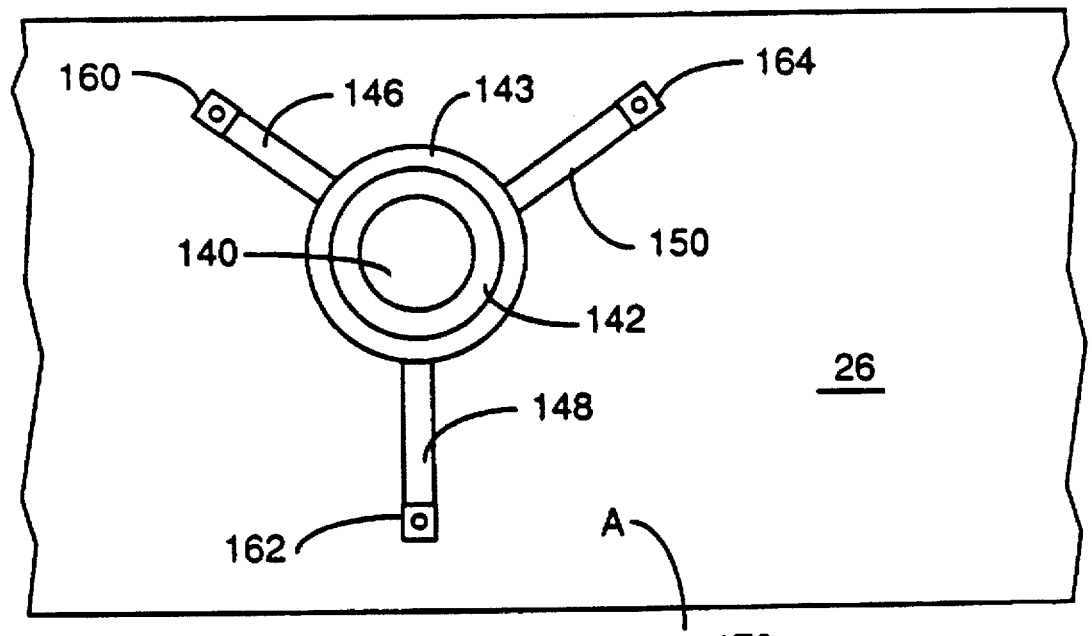
FIG. 6 is a plan view of one embodiment of a test tube clamping means secured to a carrier.

FIG. 6 is a schematic top plan view of a form of clamp member 138 wherein a central opening 140 is surrounded by a resilient collar 142, disposed within a rigid collar 143 with the opening of such size that the receptacles 120–128, are resiliently maintained in intimate contact therewithin so as to resist movement of the receptacles 120–128 with respect to clamp members 130–138. Three angularly downwardly projecting legs 146, 148, 150 terminate, respectively, in outwardly projecting feet 160, 162, 164, which are secured to the underlying carder 26 by suitable fasteners (not shown), such as screws passing through openings in the feet 160, 162, 164. It will be appreciated, therefore, that the test tubes 120–128 may be inserted into the clamps with the slides oriented in general alignment with the direction of travel of the carrier member 26 and the resultant movement being effected by the stepper motor 70 (FIG. 1) so as to cause the desired dwell for readings by the light scatter sensing means 60, 62. A letter "A" 170 has been permanently affixed to carrier member 26 provided adjacent the clamp to facilitate tube identification. Each carrier would be provided with a unique identifier as by a letter, a number, an alphanumeric or other identifying means.

Figure 7:
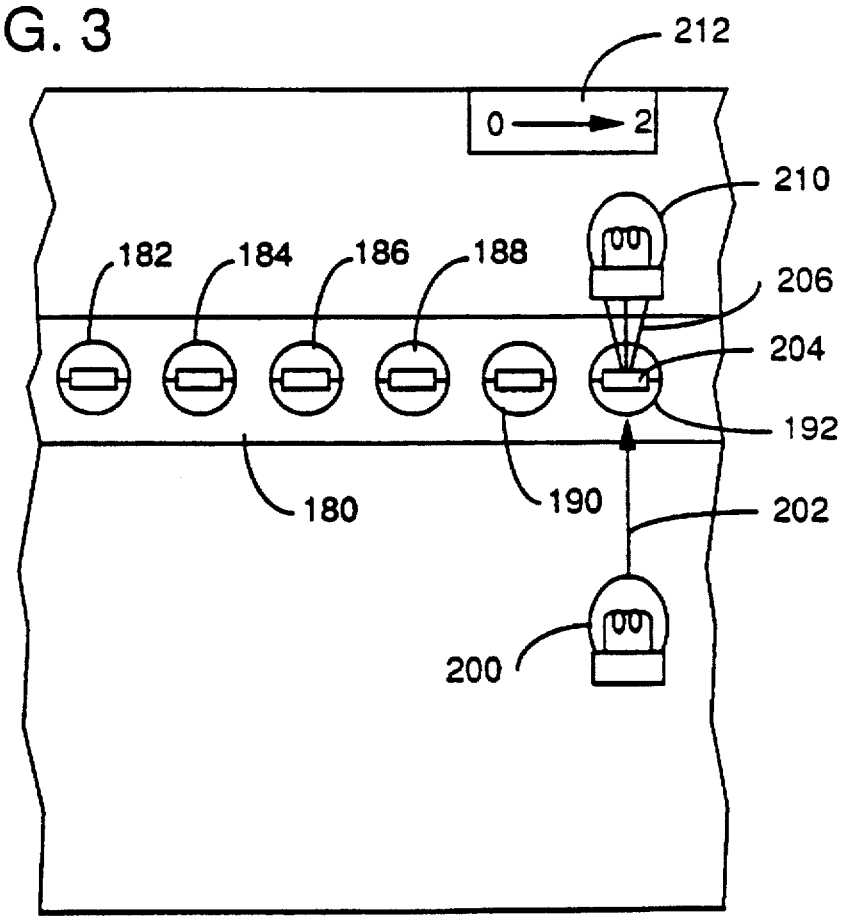
FIG. 7 a schematic illustration in plan of a portion of the scattered light sensing apparatus and associated slide moving means.

If desired, in lieu of computer means and output means 66, a direct readout gauge may be employed. Referring to FIG. 7, there is shown an embodiment of the invention wherein the carrier member 180 has a plurality of slide containing tubes 182, 184, 186, 188, 190, 192 (even numbers only) secured thereto. A light source 200 emits a light beam 202 which upon impinging upon slide 204 produces scattered light 206 which is received by photoelectric cell 210. The photoelectric cell 210, in turn, is operatively associated with a digital readout on digital reader screen 212, which provides an indication of the degree of growth of the paraffinophilic microorganism on the slide. The number on the screen may, for example, range from 0 to 2 and be directly related to the degree of growth on a slide.

While it has been mentioned hereinbefore that a positive control slide having full growth could be employed, a negative slide having no growth could be employed alone or, as in the preferred embodiment, in combination with a positive growth control slide. The positive growth control slide might be assigned a value of "one" and the negative control slide may be assigned the value of "two" corresponding to no growth of the paraffinophilic microorganism. Both control slides will preferably be employed with each test run directly or through computer storage of information related to the control slides and comparison of readings of test slides therewith.

EXAMPLE 1

Tests were performed to determine the antibiotic sensitivity for MIC Value in µg/ml of ciprofloxacin-HCl in paraffin slide culture and microliter assays for MAI. The results of this test are shown in TABLE 1.

TABLE I

| Strains | Paraffin Slide Culture Exp. Series II MIC | Days to Confluency | Exp. Series III MIC | Days to Confluency |
|---|---|---|---|---|
| 1 | 3.6 | 9 | 3.6 | 7 |
| 2 | 18.2 | 9 | 14.5 | 8 |
| 3 | NG* | NG | 3.6 | 8 |
| 4 | 3.6 | 10 | 3.6 | 9 |
| 5 | 7.3 | 9 | 7.3 | 8 |
| 6 | 3.6 | 10 | 7.3 | 9 |
| 7 | 3.6 | 10 | 7.3 | 8 |
| 8 | 3.6 | 9 | 3.6 | 8 |
| 9 | 3.6 | 10 | 3.6 | 8 |
| 10 | 14.5 | 7 | 14.5 | 6 |
| 11 | 7.3 | 7 | 7.3 | 6 |
| 12 | 10.9 | 7 | 7.3 | 6 |
| 13 | 18.2 | 8 | >18.2 | 7 |
| 14 | 18.2 | 7 | 14.5 | 7 |
| 15 | 7.3 | 7 | 7.3 | 7 |
| 16 | 7.3 | 7 | 3.6 | 6 |

*NG = No Growth

This table shows for each strain the MIC and days to confluency. This data would, therefore, provide prompt guidance to medical personnel regarding the MIC of ciprofloxacin-HCl which could be employed to inhibit growth of MAI.

EXAMPLE 2

This series of tests was similar to the tests of Example 1 except that the antimicrobial agent was amikacin. The results are shown in TABLE 2.

TABLE 2

| Strains | Paraffin Slide Culture Exp. Series I MIC | Days to Confluency | Exp. Series II MIC | Days to Confluency | Exp. Series III MIC | Days to Confluency |
|---|---|---|---|---|---|---|
| 1 | >16.0 | 7 | >16.0 | 7 | 3.2 | 5 |
| 2 | >16.0 | 7 | 12.0 | 7 | 3.2 | 5 |
| 3 | 6.4 | 8 | 6.4 | 9 | 6.4 | 12 |
| 4 | 3.2 | 8 | 6.4 | 5 | 3.2 | 6 |
| 5 | 6.4 | 7 | 3.2 | 5 | 3.2 | 5 |
| 6 | 12.0 | 7 | 3.2 | 5 | 3.2 | 5 |
| 7 | NG* | NG | 6.4 | 5 | 6.4 | 5 |
| 8 | >16.0 | 7 | >16.0 | 7 | 3.2 | 5 |
| 9 | 12.0 | 8 | 3.2 | 6 | 3.2 | 7 |
| 10 | 6.4 | 6 | 6.4 | 6 | 3.2 | 5 |
| 11 | 7.3 | 5 | 9.6 | 6 | 6.4 | 5 |
| 12 | 3.2 | 5 | 6.4 | 6 | 6.4 | 5 |
| 13 | 3.2 | 6 | 9.6 | 6 | 6.4 | 6 |
| 14 | 9.6 | 5 | >16.0 | 6 | 6.4 | 5 |
| 15 | 6.4 | 5 | 6.4 | 6 | 3.2 | 5 |
| 16 | 6.4 | 5 | 9.6 | 6 | 3.2 | 5 |

*NG = No Growth

These results would be employed to employ amikacin in treatment of a patient.

The slide containing receptacles may be introduced into and removed from the carrier member 26, 180 and clamps manually or, if desired, by automated means.

It will be appreciated, therefore, that by the use of the automated transport and light scatter sensing means, more rapid determination of antibiotic sensitivity thereto, may be effected. These rapid results can be employed to provide more prompt and efficient treatment of a patient.

The slides employed may, if desired, be miniaturized having a width of about 0.5 cm to 2.5 cm, a height of about 2 cm to 5 cm, and a thickness of about 1 mm to 2.5 mm.

Whereas particular embodiments of the invention have been described herein for purposes of illustration, it will be evident to those skilled in the art that numerous variations of the details may be made without departing from the invention as defined in the appended claims.

We claim:

1. A method of automatically testing the sensitivity of a paraffinophilic microorganism to different antimicrobial agents and concentrations thereof comprising:

providing a plurality of receptacles each containing an amount of liquid medium, an antimicrobial agent to be tested and said paraffinophilic microorganism to be tested;

placing in each of said receptacles a slide containing a paraffin coating;

automatically sequentially detecting paraffinophilic microorganism growth or the lack thereof on each of said slides by employing a light scatter sensing means; and determining from said detection by said light scatter sensing means of said paraffinophilic microorganism growth or the lack thereof the sensitivity of said paraffinophilic microorganism to said antimicrobial agent to be tested.

2. The method of claim 1 including employing as said light scatter sensing means a nephelometer.

3. The method of claim 2 including said nephelometer includes a display screen for displaying information related to said paraffinophilic microorganism growth or lack thereof on each said slide.

4. The method of claim 3 including employing a control receptacle containing (i) a liquid medium, (ii) said paraffinophilic microorganism to be tested and (iii) a control paraffin coated slide, said control receptacle containing no antimicrobial agent whereby paraffinophilic microorganism growth on said control paraffin coated slide can be compared to said paraffinophilic microorganism growth on slides containing a paraffin coating which are placed into said receptacles containing said antimicrobial agent.

5. The method of claim 4 including in addition to said negative control slide employing a-positive slide to calibrate said nephelometer.

6. The method of claim 3 including employing computer means operatively associated with said nephelometer to process said information relating to said paraffinophilic microorganism growth or lack thereof on each said slide.

7. The method of claim 6 including automatically sequentially moving each said slide to operative relationship with said nephelometer, and causing said slide to dwell in operative position while said nephelometer obtains data from scattered light emerging from said slide.

8. The method of claim 7 including orienting said slides in general alignment with the path of travel of said slides by said nephelometer.

9. The method of claim 8 including restraining said slides in said orientation within said receptacles, and effecting translational movement of said receptacles by said nephelometer while resisting rotational movement of said receptacles.

10. The method of claim 6 including
effecting said automated testing of said test slides at the rate of about 6 to 30 per minute.

11. The method of claim 1 including
effecting said automatic testing by sequentially moving said slides into operative relationship with said light scatter sensing means.

12. The method of claim 1 including
employing test tubes as said receptacles.

13. The method of claim 1 including
obtaining said paraffinophilic microorganism from a body specimen.

* * * * *

UNITED STATES PATENT AND TRADEMARK OFFICE
CERTIFICATE OF CORRECTION

PATENT NO. : 5,726,030

DATED : March 10, 1998

INVENTOR(S) : Robert A. Ollar & Mitchell S. Felder

It is certified that error appears in the above-identified patent and that said Letters Patent is hereby corrected as shown below:

Column 4, line 1, change "them" to -- there --.

Column 4, line 41, change "carder" to -- carrier --.

Column 6, line 24, change "carder" to -- carrier --.

Column 3, line 22, after "FIG. 7" insert -- is --.

Signed and Sealed this

Twenty-eighth Day of September, 1999

Attest:

Q. TODD DICKINSON

Attesting Officer

Acting Commissioner of Patents and Trademarks